United States Patent [19]

Levin

[11] 4,250,889
[45] Feb. 17, 1981

[54] HEARTBEAT OCCURRENCE DETECTOR

[76] Inventor: Kenneth M. Levin, 14 Anchorage Ct., San Rafael, Calif. 94903

[21] Appl. No.: 17,020

[22] Filed: Mar. 2, 1979

[51] Int. Cl.³ ............................................... A61B 5/04
[52] U.S. Cl. ..................................... 128/708; 128/901
[58] Field of Search ............... 128/696, 702, 703, 704, 128/708, 901

[56] References Cited

U.S. PATENT DOCUMENTS

| | | | |
|---|---|---|---|
| 3,267,934 | 8/1966 | Thornton | 128/704 |
| 3,699,946 | 10/1972 | Michel | 128/702 |
| 3,731,672 | 5/1973 | McIntosh | 128/703 |
| 3,868,967 | 2/1975 | Ekstrom | 128/704 |

Primary Examiner—William E. Kamm
Attorney, Agent, or Firm—Townsend and Townsend

[57] ABSTRACT

Apparatus for monitoring the heartbeat of a person by screening the occurrence of a heartbeat from artifact to produce a signal indicative of the heartbeat occurrence. Screening circuitry detects the R-wave and S-wave peaks of an ECG signal, delays the R-wave peak detection and compares the delayed R-wave peak detection to the S-wave peak detection for coincidence to determine a heartbeat occurrence. Binary counting circuits compare the elapsed time between any two immediately successive heartbeat occurrence indications to determine heartbeat rate. Display apparatus, operably coupled to the counting circuits, provides indicia of the relative heartbeat rate.

5 Claims, 9 Drawing Figures

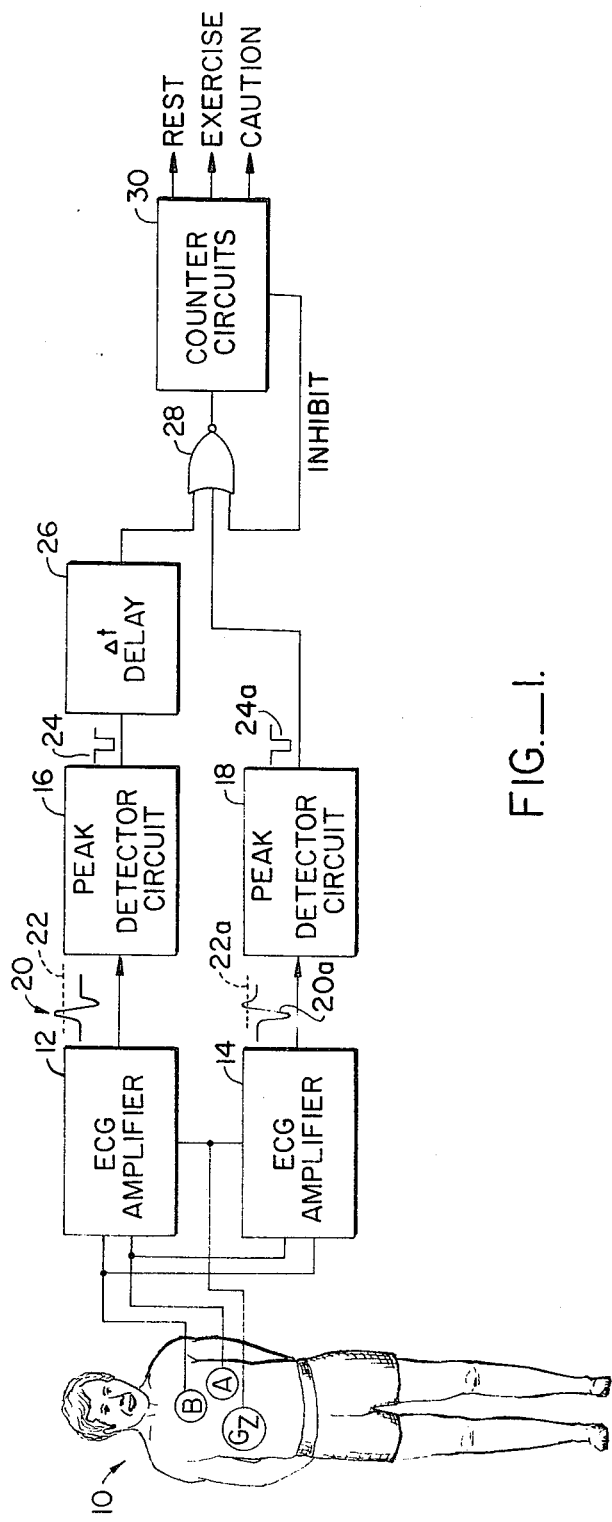
FIG._1.

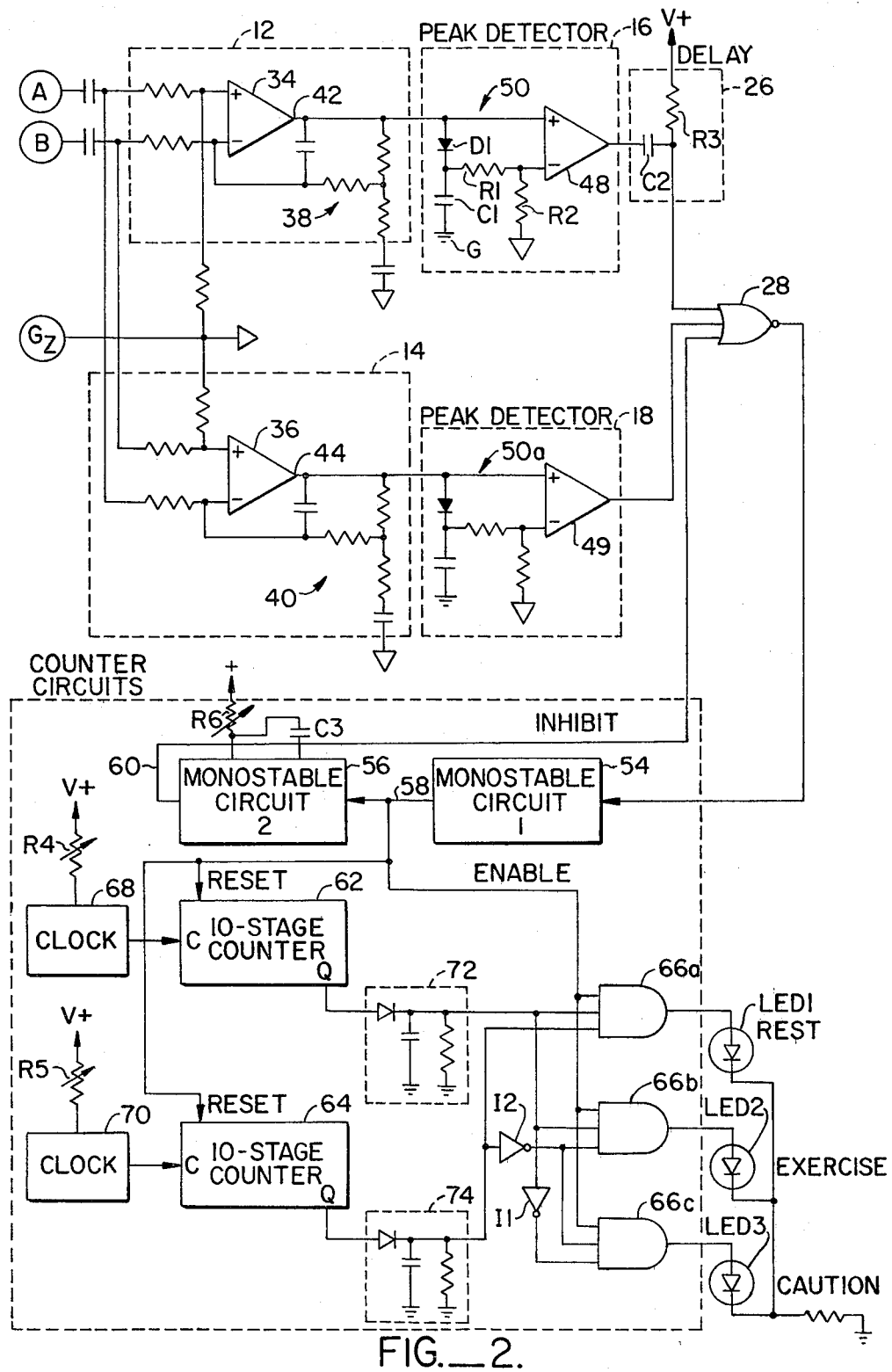
FIG._2.

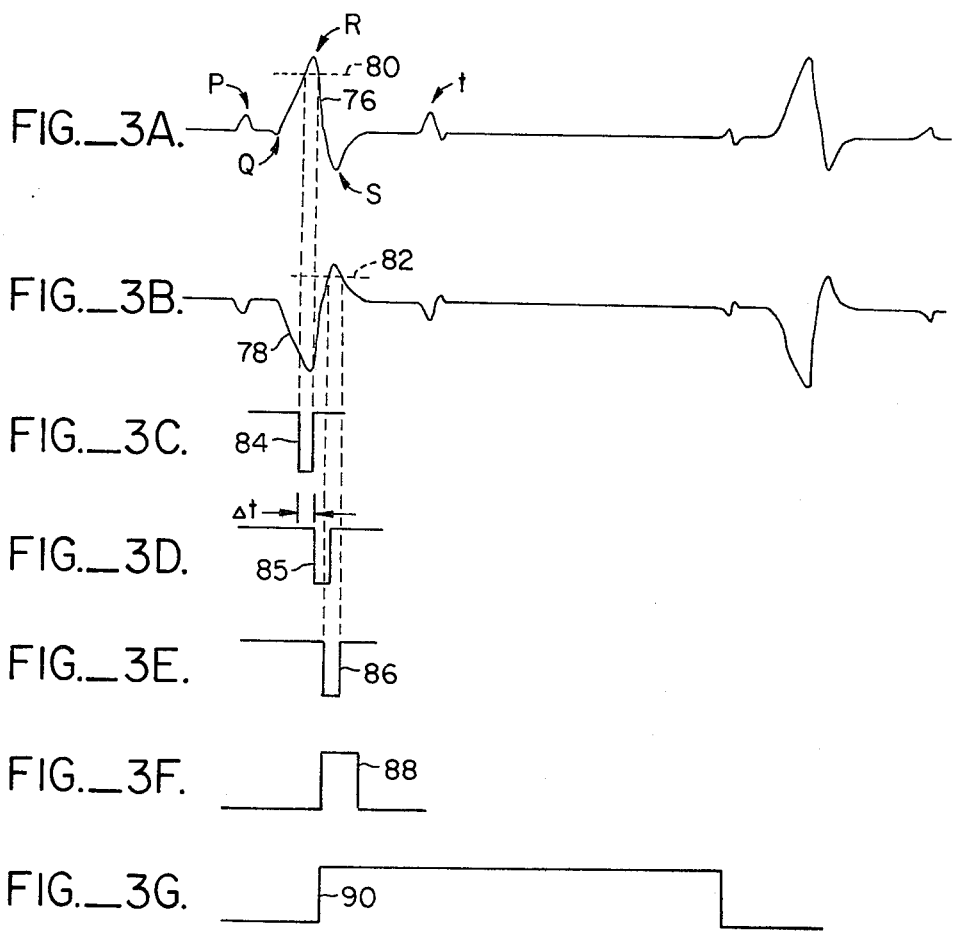

HEARTBEAT OCCURRENCE DETECTOR

The present invention relates to monitoring cardiac-produced signals and more particularly to a cardiac monitoring device that includes circuitry for screening and/or eliminating undesirable artifact, to produce a signal indicative of a heartbeat and for monitoring said heartbeat indications.

BACKGROUND OF THE INVENTION

It is well known that expansion and contractions of muscle produce electrical signals that circulate upon the surface of a person's skin. Perhaps the most common are the expansions and contractions of the cardiac muscle, which are typically referred to as ECG signals. These ECG signals exhibit particular waveforms containing several distinct characteristics for each heartbeat. These characteristics, generally labeled P, Q, R, S and T, according to common medical usage, have allowed medical science to monitor a person's heartbeat or heartbeat count.

Of the three positive peaks of a single heartbeat signal, the P, R and T pulses, it is usually the R peak that is the largest. Since it is necessary that ony one peak be detected for each heartbeat, a threshold detector can be employed in the simple case to distinguish between P and T waves, on the one hand, and R waves on the other. Accordingly, the R-wave peaks are available to trigger the threshold detector to generate heartbeat count and are often so used.

At times, however, the P and/or T waves are taller than the R waves. In this instance utilization of a simple comparator operating directly on the unfiltered ECG waveform becomes erratic. One attempt at controlling this problem is be employing some form of filtering to attenuate the P and T waves in relation to the R waves, since R waves contain higher frequencies than other parts of the ECG waveform. Thus, for example, high-pass filters are used to attenuate P and T waves more than R waves. However, this solution is not always satisfactory. Additionally, pulse width discrimination is also used to detect the R wave and identify the ECG waveform from other muscle activity.

However, as noted at the outset, all muscle tissue will emit electrical signals when expanding or contracting, the heart being only one of the many muscle groups of a person's body. Since other muscle groups will also emit electrical signals, it is desirable that the person remain relatively motionless while an ECG waveform is being obtained—particularly if the fidelity of the desired ECG waveform is to be as accurate as possible.

When a person is in motion, however such as when exercising, the problem of monitoring the person's heartbeat becomes extremely difficult; the reason being that sensors placed on the person detecting the ECG signal also receive electrical signals produced by the other expanding and contracting muscles of the body —and other motion signals—termed "artifact". The heretofore known practices of limiting the frequency response characteristics of the ECG waveform and/or rejecting artifact by amplitude discrimination or pulse width discrimination to identify each heartbeat has been found to be generally insufficient, even when these techniques are used in combination.

Therefore, it is desirable that additional techniques be found to allow accurate monitoring of a person's heartbeat during exercise to allow one to obtain reliable heartbeat information in the presence of such artifact. This is particularly true if the person wishes to exercise his or her cardiovascular system, yet keep his or her heartbeat within predetermined limits.

SUMMARY OF THE INVENTION

The present invention, therefore, provides apparatus that monitors a person's heartbeat during exercise. The invention allows the heartbeat or ECG signal to be detected even in the presence of motion, muscle or other artifact.

According to the present invention, the ECG waveform is applied to positive and negative peak detector circuits which recognize excursions of the ECG waveform relative to predetermined DC levels and provide output signals indicative of such excursions beyond the DC levels. The output signal of the positive peak detector circuit is delayed a predetermined period of time and applied, with the output signal of the negative peak detector circuit, to a coincidence circuit for comparison. The coincidence circuit produces a signal that is indicative of a heartbeat. This signal is applied to counter circuitry and used to establish the relative beat-to-beat time period of the monitored heartbeat to determine whether the heartbeat rate repetition frequency is within predetermined limits. Indicia, responsive to the counter and coincidence circuits, provide the user with heartbeat information.

Thus, it should be evident that the present invention provides a number of advantages not heretofore obtained by presently available heartbeat monitoring apparatus. First, the invention operates to reject troublesome artifact that can seriously impair or obscure heartbeart monitoring. This, in turn, allows the invention to monitor heartbeat activity while a person is exercising. The user (or his supervising physician) can set limits upon the stress placed upon his or her cardiovascular system through exercise and, while exercising, be assured that the cardiovascular system is sufficiently stressed without exceeding those limits.

For a fuller understanding of the nature and advantages of the invention, reference should be had to the ensuing detailed description taken in conjunction with the accompanying drawings.

BRIEF DESCRIPTION OF THE DRAWINGS

FIG. 1 is a block diagram of the heart monitoring apparatus according to the present invention;

FIG. 2 is a more detailed schematic of the block diagram of FIG. 1; and

FIGS 3A–3G illustrate typical waveforms involved in the operation of the apparatus of FIG. 2.

DETAILED DESCRIPTION OF THE INVENTION

An illustrative embodiment of the invention, in block diagram form, is shown in FIG. 1. Standard ECG amplifiers 12 and 14 are connected to a person 10 in the conventional manner via heartbeat sensing transducers A and B. The sensors are placed on the person 10 for picking up the varying cardiac potential and are coupled to the inputs of the ECG amplifiers 12 and 14. A third transducer $G_z$ is utilized as a reference electrode and is also coupled to the ECG amplifiers 12 and 14.

The electrical ECG signals coupled to the ECG amplifiers 12 and 14 are differentially amplified to provide two substantially equal but complementary output signals that are communicated to peak detectors 16 and 18.

The peak detectors 16 and 18 produce output pulses when the electrical signals applied thereto exceed predetermined DC levels. Thus, when the difference signal provided by ECG amplifier 16, illustrated in FIG. 1 as waveform 20, exceeds a DC level 22, the peak detector 16 produces a pulse 24 that is coupled via a delay circuit 26 to a coincidence gate 28. Similarly, the peak detector 18 produces an output pulse 24a when the (inverted) waveform 20a exceeds a predetermined DC level 22a. In this manner, the R and S wave portions of the received ECG signal are detected, compared and used to generate a pulse—the output of the coincidence gate 28—that is indicative of heartbeat occurrence yet free of troublesome artifact that may also have been present in the ECG signals.

Coincidence gate 28 is connected to counter circuits 30. The signal provided by coincidence gate 28 is effectively compared by counter circuits 30 to predetermined time intervals to determine whether the heartbeat rate being monitored is above, below or within a specified range of preferred cardiac activity. The results of this determination are REST, EXERCISE and CAUTION signals which are displayed to the user via light-emitting diodes LED1–LED3 (FIG. 2). Thus, for example, the user may be informed his or her heartbeat rate is below a first rate—indicating a resting heartbeat (e.g., 80 beats per minute)—or, alternatively, that the user's heartbeat is above a predetermined limit and caution is advised.

Referring now to FIG. 2, there is shown a more detailed schematic drawing of the block diagram of the invention illustrated in FIG. 1. As shown, the ECG amplifiers 12 and 14 include differential amplifiers 34 and 36, respectively. In turn, each of the differential amplifiers 34 and 36 include a conventional resistor/capacitor 38 and 40 configuration to limit the bandwidth of each amplifier to approximately 10–30 Hz to provide first artifact discrimination feature. The heartbeat sensing transducer A is applied to the positive input of the differential amplifier 34 and amplified relative to the signal obtained by the heartbeat sensing transducer B, which is applied to the negative input of the differential amplifier circuit 34. Similarly, the electrical activity obtained by the heartbeat sensing transducers A and B are applied to the differential amplifier circuit 36 in reverse configuration. Thereby, the electrical signals obtained by the heartbeat sensing transducers A and B appear at the respective amplifier outputs 42 and 44 of differential amplifiers 34 and 36 as two filtered, complementary difference signals.

The outputs 42 and 44 of the differential amplifiers 34 and 36, respectively, are coupled to the peak detectors 16 and 18. Each peak detector is essentially identical in configuration and, therefore, only the peak detector 16 will be described, it being remembered that the description applies essentially also to the peak detector 18. Any difference between the two will be noted.

The peak detector 16 includes a comparator 48 to which is coupled the output 42 of differential amplifier 34. A DC level-setting circuit 50 interconnects the output 42 and amplifier 48. The DC level-setting circuit 50 comprises a diode D1, voltage-divider resistors R1 and R2, and capacitor C1. The resistors R1 and R2 interconnect diode D1 with the reference heartbeat sensing transducer $G_z$. The capacitor C1 interconnects the diode D1 with the circuit ground G. The level-setting circuit 50, in effect, holds the output 42 at a predetermined DC level. When the signal provided by the amplifier 34 exceeds the predetermined DC level set by the level-setting circuit 50, the comparator 48 will generate a (negative-going) pulse.

The DC levels for peak detectors 16 and 18 are set by the threshold voltage of D1, in combination with the voltage divider network formed by the resistors R1 and R2. The capacitor C1 acts as a memory to expand the width of narrower pulses.

The output of the differential amplifier 48 is applied to the delay circuit 26 comprising capacitor $C^2$ and resistor R3 in a simple differentiator configuration. The signal produced by the peak detector 16 is then communicated from the delay circuit 26 to the coincidence (NOR) gate 28. Coincidence gate 28 also receives the signal provided by the peak detector 18 which, as noted above, operates essentially the same as peak detector 16.

The output of coincidence gate 28 is applied to, and used to trigger, a first monostable circuit 54. The pulse produced by the monostable 54 is communicated to a second monostable circuit 56 via output line 58. The output 60 of monostable 56 is coupled to an input of coincidence gate 28 and used as an inhibit signal of a predetermined time period, as will be described more fully below.

The output 58 of monostable 54 is also used as a RESET signal and is coupled to the reset inputs of 10-stage (binary) counters 62 and 64. Applied to the clock (c) inputs of each 10-stage counter 62, 64 are digital pulses provided by variable clocks 68 and 70. Variable resistors R4 and R5 allow the frequency of each clock 68 and 70, respectively, to be adjusted and set as desired.

The Q outputs of the last or tenth stage of counter 62 is a memory circuit 72 and from there to coincidence gates 66a and 66b. The memory circuit 72 is coupled to coincidence gate 66c via inverter I1. In similar fashion, the Q output of the last or tenth stage of counter 64 is coupled, via memory circuit 74, to coincidence gate 66a; and, via both the memory circuit 74 and inverter I2, to coincidence gates 66b and 66c. The outputs of coincidence gates 66a-66c are applied to light-emitting diodes LED1–LED3.

The frequency of operation of clocks 68 and 70 provides a time base, measured by the 10-stage counters 62 and 64, against which the user's beat-to-beat heartbeat interval is measured. Thus, a first of two successive heartbeat indicating signals from coincidence gate 28 will cause, via monostable 54, the 10-stage counters 62 and 64 to be reset to their zero or initial states. The 10-stage counters 62 and 64 then commence counting the pulses provided by the clocks 68 and 70 until the next succeeding heartbeat indicating signal is communicated by coincidence gate 28. At the same time, the succeeding heartbeat indicating signal (e.g., the ENABLE signal provided by monostable 54) is compared to the states of the Q outputs of 10-stage counters 62 and 64 by coincidence gates 66a–66c. Depending upon the states of the Q outputs of the 10-stage counters 62 and 64, one of the indicators LED1–LED3 will be activated by the corresponding coincidence gate 66a–66c upon appearance of the ENABLE signal from monostable 54.

A user is thereby provided with information as to his or her heartbeat—relative to predetermined standards. This will be discussed further below. For example, a heartbeat rate that is less than the frequency of operation of the clocks 68 and 70 divided by 512 is determined by coincidence of the inputs of coincidence gate 66a: The Q outputs of both 10-stage counters 62 and 64 being a logical one together with appearance of the ENABLE signal on output line 58 of the monostable circuit 54. Alternately, appearance of the ENABLE signal before the Q outputs of the 10-stage counters 62 and 64 have achieved a logical one will indicate a heartbeat rate that is above that limit set by the frequency of oscillation of clock 68. This latter situation is detected by the coincidence gate 66c. A heartbeat rate between these two limits is detected by the coincidence gate 66b, indicating that the heartbeat rate is within the desired limits. Depending upon which of the coincidence gates 66a–66c is activated upon occurrence of the ENABLE signal from monostable 54, one of the indicators LED-1–LED3 with REST, EXERCISE and CAUTION signals, indicating a monitored heartbeat below, within or above the limits of the clock/counter time bases.

Referring now to FIG. 3, the operation of the invention will be described. The heartbeat sensing transducers A, B and reference transducer $G_z$ are placed upon the skin of the person 10 (FIG. 1). Preferably, the heartbeat sensing transducers A and B are positioned so that the heart of the person 10 is positioned approximately between them.

So located, the heartbeat sensing transducers A and B will sense and communicate electrical signals produced by cardiac activity to the ECG amplifiers 12 and 14. Additionally, the heartbeat sensing transducers will also receive artifact electrical signals produced by other muscle tissue. Thus, the signals received by the ECG amplifiers 12 and 14 are composite ECG signals, containing both the desired heartbeat information and unwanted artifact. These composite signals are differentially amplified by differential amplifiers 34 and 36, appearing at the outputs 42 and 44 as the electrical signals 76 and 78, illustrated in FIGS. 3A and 3B. As illustrated in FIGS. 3A and 3B, the signals provided by the differential amplifiers 34 and 36 are the complement of one another.

The electrical signals 76 and 78 are respectively applied to the peak detectors 16 and 18. As mentioned above, the comparator 48 of the peak detector circuit will provide an output when the electrical signal appearing on the output line 42 exceeds the DC level, represented in FIG. 3A by the dotted line 80, set by the level-setting circuit 50. Of course, the DC level 80 would be set to detect the R-wave peak, but would also detect any artifact that was not filtered by the bandwidth discrimination of the circuitry of differential amplifier 34. Signals that do exceed the DC level 80, such as the R-wave peak of waveform 76, cause the comparator 48 to provide a negative-going pulse 84 (FIG. 3C).

Similarly, the electrical signal appearing at output 44 of the differential amplifier 36 is applied to the comparator 49 of the peak detector 18. When the electrical signal appearing on the output 44 exceeds the DC level set by the level circuit 50a (indicated in FIG. 3B by the dotted line 82), the comparator 44a will provide an output in the form of the negative-going pulse 86 (FIG. 3E).

Thus, the ECG waveform indicative of cardiac activity, which typically includes the R and S-wave peaks illustrated in FIG. 3A, will cause the respective comparators 48 and 49 to produce the negative-going pulses 84 and 86 shown in FIGS. 3C and 3E. The pulse 84 provided by the comparator 48 is first applied to the delay circuit 26, delayed a predetermined amount of time ($\Delta t$), and then communicated as a delayed pulse 85 (FIG. 3D) to coincidence gate 28. The second input of coincidence gate 28 receives the pulse 86 from comparator 49.

Thus, if the electrical activity detected by the heartbeat sensing transducers A and B include a first positive-going pulse (the R-wave peak) followed, a predetermined amount of time, by a negative-going pulse (the S-wave peak) and such pulses exceed predetermined DC levels, such activity is determined to be a heartbeat. In this manner, other electrical activity included in the ECG waveform is filtered.

Coincidence between the two signals provided by the comparators 48 (via delay circuit 26) and 49 (together with the INHIBIT signal from monostable 56) set at a logic zero will cause coincidence gate 28 to issue a signal which, in turn, is communicated to and fires the monostable 54. The monostable 54 thereupon provides, on output lines 58, a positive RESET/ENABLE signal 88, illustrated by FIG. 3F. The RESET/ENABLE signal 88 is used to trigger monostable 56 which, in turn, fires to produce a positive INHIBIT signal 90 (FIG. 3G) on output line 60. The INHIBIT signal is communicated to a third input of the coincidence gate 28.

The INHIBIT signal 88 is used to block, for a predetermined time period, further signals indicative of a heartbeat being produced by coincidence gate 28. In effect, the INHIBIT signal produced by monostable 56 functions to provide further filtering of artifact which could be interpreted by the invention as a heartbeat pulse. For example, assume the time the INHIBIT pulse 90 remains in its logic zero state is 0.3 seconds. This is equal to the time interval between two successive heartbeats for a heartbeat rate of 200 beats per minute (i.e., 60/200 = 0.3). Thus, the invention will correctly monitor heartbeat rates that are less than 200 beats per minute. For particular users, this limit (200 beats per minute) is realistic and any artifact resembling a heartbeat signal, yet would indicate a heartbeat rate higher than the 200 beats per minute maximum, is eliminated. Preferably, the time-out period of monostable is selectable; and, therefore, variable resistor/capacitor combination R6 and C3 are provided.

The RESET/ENABLE signal provided by the monostable circuit 54 is also applied to the reset inputs of the 10-stage counters 62 and 64. Each counter, which had been counting clock pulses provided by clock 68 and 70 is reset to its initial or zero state by the RESET signal. If either of the Q outputs of the respective 10-stage counters 62 and 64 had become a logic one, indicating the presence of one or both limits, such information would be temporarily stored by the storage circuit 72 or 74, respectively. The binary state of the Q outputs of the 10-stage counters 62 and 64 (which, it will be remembered, are the Q outputs of the last or tenth stage of each counter) at the time of occurrence of the RESET signal provided by the monostable circuit 54, indicate one of three heartbeat conditions: (1) If both Q outputs of the 10-stage counters 62 and 64 are a logic zero, the heartbeat rate is greater than the limit set by the frequency of oscillation, divided by 512 (i.e., $2_9$), of clocks 68 and 70; (2) if the Q outputs of the 10-stage counters 62 and 64 are a logic one and a logic zero, respectively, the heartbeat rate is within a predetermined range; and (3) if both Q outputs of the 10-stage counters 62 and 64 are logic ones, the heartbeat rate is less than the predetermined minimum set by the frequency of oscillation, divided by 512, of the clock 70.

For example, assume that the variable resistor R4 has set the frequency of oscillation of clock 68 to be 1280

Hz. When the 10-stage counter 62 counts the pulses produced by clock 68, a first time base of 0.4 seconds (512 ÷ 1280 Hz) is established by transition from a logic zero to a logic one of the Q output of the 10-stage counter 62; a time base that is measured from detection of a heartbeat indication. The 0.4 second time base tranlates to a heartbeat rate limit of 150 beats per minute.

Now assume that the variable resistor R5 is set so that the frequency of oscillation of clock 70 is 1024 Hz. The occurrnece of the output of the 10-stage counter 64 becoming a logic one determines, from the reset state, a time base of 0.5 seconds—which translates to a heartbeat rate of 120 beats per minute.

With the variable resistors R4 and R5 set as described, the counter circuit 30 now has two predetermined time-base standards against which the beat-to-beat interval of a person's cardiac activity may be compared. Thus, for example, if the time period between any two successive heartbeat indications is less than the time from reset of the 10-stage counters 62 and 64 (caused by the first of the two indications) to Q=one, the heartbeat rate is determined as being greater than 150 beats per minute. On the other hand, if the Q output of the 10-stage counter 64 is a logic one when a heartbeat is detected, the rate is established as being less than 120 beats per minute. Similarly, if the Q outputs of the 10-stage counters 62 and 64 are a logic one and logic zero, respectively, when the second, succeeding heartbeat is detected, it is established that the heartbeat rate is somewhere between 120 and 150 beats per minute.

As can be seen in FIG. 2, these conditions are detected by the coincidence gates 66a–66c. The ENABLE signal provides an indication of heartbeat presence. The Q outputs of the 10-stage counters 62 and 64 are coupled to the coincidence gates 66a–66c via the memory circuits 72 and 74. Depending upon the particular condition of the 10-stage counters 62 and 64 when the ENABLE signal appears, one of the indicators LED-1–LED3 will be activated by its corresponding coincidence gate 66a–66c. Thus, if the heartbeat rate is less than 120 beats per minute in the above example, the LED1 indicator will be activated (both Q outputs of the 10-stage counters 62 and 64 are logic ones when the ENABLE signal appears); if the heartbeat rate is greater than 120 beats per minute but less than 150 beats per minute the LED2 indicator will be activated (the Q output of the 10-stage counter 62 is a logic one but the Q output of the 10-stage counter 64 is still a logic zero when the ENABLE signal appears); and the indicator LED3 will be activated when neither Q output of the 10-stage counters 62 and 64 have yet become a logic one when the ENABLE signal occurs.

In summary, therefore, there has been disclosed apparatus for discriminating between a person's heartbeat and other artifact to produce a signal that is used to monitor the person's heartbeat rate. By peak detecting the R-wave and S-wave peaks, delaying the former a predetermined period of time and monitoring for coincidence, a significant amount of artifact activity is filtered. This allows one to monitor heart activity in the presence of motion such as exercise.

What is claimed is:

1. Apparatus for detecting a heartbeat occurrence in an electrocardiographic waveform containing artifact information, the heartbeat occurrence being represented by at least first and second pulses, the first and the second pulses respectively having amplitudes of at least a first and a second absolute value, and for providing an output signal indicative of said occurrence, the apparatus comprising:
   means responsive to said waveform for detecting the first and the second values and for providing first and second signals indicative of said first and second pulses;
   means coupled to said detecting means for delaying said first signal a predetermined amount of time;
   means coupled to said detecting means and said delaying means and responsive to coincidence between said second signal and said delayed first signal to generate said output signal; and
   means coupled to said coincidence means and responsive to said output signal for inhibiting coincidence between said second signal and said delayed first signal for a second predetermined time period, the second predetermined time period corresponding to a predetermined maximum heartbeat rate.

2. The apparatus of claim 1, wherein said delaying means includes a differentiating circuit.

3. The apparatus of claim 1, wherein the inhibiting means includes pulse generating means responsive to said output signal for generating an inhibit signal of said second predetermined time period and for communicating said inhibit signal to said coincidence means, the pulse generating means including means for varying the second predetermined time period.

4. The apparatus of claim 1, wherein the detecting means includes respective first and second peak detecting means for detecting peaks of the first and second pulses.

5. Apparatus for detecting a heartbeat occurrence of a person including, for each such occurrences at least an R-wave and an S-wave peak, and for providing an output signal indicative of said occurrence, the apparatus comprising:
   transducer means coupled to said person for producing at least a first and a second electrocardiographic waveform;
   means coupled to said transducer means for receiving said electrocardiographic waveforms and for detecting said R-wave and said S-wave peaks to produce therefrom first and second binary signals, respectively representative of said detected R-wave and S-wave peaks;
   means for delaying said first binary signal a predetermined period of time;
   comparing means responsive to coincidence between said first delayed signal and said second signal to produce therefrom said output signal; and
   pulse generating means responsive to said output signal for generating an inhibit pulse to inhibit coincidence between said delayed first signal and said second signal for a second predetermined time period, said second predetermined time period corresponding to a predetermined maximum heartbeat occurrence rate.

* * * * *